US012636004B2

(12) United States Patent
Binmoeller et al.

(10) Patent No.: US 12,636,004 B2
(45) Date of Patent: May 26, 2026

(54) LOCK-CUT MECHANISM AND MEDICAL SUTURING DEVICE

(71) Applicants: MICRO-TECH (NANJING) CO., LTD., Pukou District Nanjing (CN); Kenneth F. Binmoeller, Rancho Santa Fe, CA (US)

(72) Inventors: Kenneth F. Binmoeller, Rancho Santa Fe, CA (US); Hongyan Jin, Jiangsu (CN); Xiaojun Ma, Jiangsu (CN)

(73) Assignees: MICRO-TECH (NANJING) CO., LTD., Jiangsu (CN); Kenneth F. Binmoeller, Rancho Santa Fe, CA (US)

( * ) Notice: Subject to any disclaimer, the term of this patent is extended or adjusted under 35 U.S.C. 154(b) by 143 days.

(21) Appl. No.: 18/797,435

(22) Filed: Aug. 7, 2024

(65) Prior Publication Data

US 2025/0057525 A1      Feb. 20, 2025

(30) Foreign Application Priority Data

Aug. 15, 2023    (CN) ......................... 202322197140.X

(51) Int. Cl.
*A61B 17/04* (2006.01)
(52) U.S. Cl.
CPC ...... *A61B 17/0467* (2013.01); *A61B 17/0401* (2013.01); *A61B 17/0491* (2013.01); *A61B 2017/0409* (2013.01)

(58) Field of Classification Search
CPC ............ A61B 17/0467; A61B 17/0469; A61B 17/0487; A61B 17/0491; A61B 2017/0488; A61B 2017/0496
See application file for complete search history.

(56) References Cited

U.S. PATENT DOCUMENTS

| | | | |
|---|---|---|---|
| 2012/0158023 A1* | 6/2012 | Mitelberg .......... | A61B 17/0485 |
| | | | 606/144 |
| 2019/0357899 A1* | 11/2019 | Gilbert .............. | A61B 17/0467 |
| 2021/0128139 A1* | 5/2021 | Deuel ............... | A61B 17/0467 |
| 2021/0128140 A1* | 5/2021 | Wales ............... | A61B 17/0487 |
| 2021/0128141 A1* | 5/2021 | Deuel ............... | A61B 17/0467 |

* cited by examiner

*Primary Examiner* — Elizabeth Houston
*Assistant Examiner* — Lindsey Bachman
(74) *Attorney, Agent, or Firm* — BCF LLP

(57) ABSTRACT

The present disclosure provides a lock-cut mechanism and a medical suturing device, which relates to the technical field of medical suturing. The lock-cut mechanism includes: a plug head, an inner tube, an outer tube, a support, and a traction member. The inner tube is detachably connected to the support. The plug head is inserted into the inner tube, and the outer tube is sleeved on the inner tube and the support. The traction member passes through the outer tube, the inner tube, and the plug head, and a distal end of the traction member is provided with a protruding head. A side wall of the inner tube is provided with a first incision, and a side wall of the outer tube is provided with a second incision.

20 Claims, 6 Drawing Sheets

LOCK-CUT MECHANISM AND MEDICAL SUTURING DEVICE

CROSS-REFERENCE TO RELATED APPLICATION

The present disclosure claims the priority of Chinese Patent Application CN 202322197140.X, titled "LOCK-CUT MECHANISM AND MEDICAL SUTURING DEVICE", filed on Aug. 15, 2023, the contents of which are incorporated herein by reference in entirety to be a part of the present disclosure.

TECHNICAL FIELD

The present disclosure relates to the technical field of medical suturing, and particularly to a lock-cut mechanism and a medical suturing device.

BACKGROUND ART

The locking and cutting operation of the suture can be performed by pulling the end cap, which causes the end cap to be inserted into the inner tube, thereby clamping and locking the suture between the end cap and the inner tube. Subsequently, by sliding the inner tube relative to the outer tube, the side openings provided in the inner tube and the outer tube are enabled to be staggered, thereby achieving the cutting action on the suture. After the suture is locked and cut, the inner tube and the end cap are left in the body. The previous lock-cut mechanisms have relatively complex structures and larger radial dimensions, which result in the lock-cut mechanism easily causing obstruction when passing through the endoscopic forceps channel.

SUMMARY

An objective of the present disclosure is to provide a lock-cut mechanism and a medical suturing device to improve the compactness of the structure of the lock-cut mechanism.

In a first aspect, the lock-cut mechanism provided in the present disclosure includes: a plug head, an inner tube, an outer tube, a support, and a traction member.

The inner tube is detachably connected to the support.

The plug head is inserted into the inner tube, and the outer tube is sleeved on the inner tube and the support.

The traction member passes through the outer tube, the inner tube, and the plug head, and a distal end of the traction member is provided with a protruding head.

A side wall of the inner tube is provided with a first incision, and a side wall of the outer tube is provided with a second incision.

In a first phase of pulling the traction member, the first incision and the second incision are aligned, and the protruding head fits with the plug head and drives the plug head to move inside the inner tube.

In a second phase of pulling the traction member, the protruding head disengages from the plug head, and the protruding head abuts the outer tube and drives the outer tube to move in an axial direction relative to the inner tube, thus causing the first incision to misalign with the second incision.

In a third phase of pulling the traction member, the traction member drives the outer tube and allows the outer tube to be sleeved onto the support, and the support separates from the inner tube.

In one optional embodiment, the inner tube is provided with a first inserting-connection part, and the support is provided with a second inserting-connection part adapted to the first inserting-connection part.

In one optional embodiment, the support is provided with a first arm rod and a second arm rod, wherein the first arm rod and the second arm rod are substantially parallel. Both the first arm rod and the second arm rod are provided with second inserting-connection parts.

In one optional embodiment, a proximal end of the outer tube is provided with a crossbeam, wherein the crossbeam is provided with a through hole coaxial with the outer tube.

The traction member passes through the through hole, and a diameter of the protruding head is larger than a diameter of the through hole.

The outer tube is provided with a first axial socket and a second axial socket, wherein the first arm rod and the second arm rod pass through the first axial socket and the second axial socket in one-to-one correspondence.

In one optional embodiment, both the first arm rod and the second arm rod are connected to a base, the crossbeam is in sliding fit between the first arm rod and the second arm rod, and the crossbeam and the base are arranged opposite to each other.

In one optional embodiment, the support is provided with a first arm rod and a second arm rod, with at least one of the first arm rod and the second arm rod provided with a snapping part that fits the inner tube. The first arm rod and the second arm rod have a tendency to be inclined in a direction close to an axis of the inner tube, thus causing the snapping part to disengage from the inner tube.

The outer tube is connected to the crossbeam, where the crossbeam is positioned between the first arm rod and the second arm rod.

In one optional embodiment, the crossbeam is provided with a through hole. The traction member passes through the through hole. A diameter of the protruding head is larger than a diameter of the through hole.

During the third phase of pulling the traction member, the protruding head abuts the crossbeam, thus causing the outer tube, along with the traction member, to slide relative to the support.

In one optional embodiment, the plug head is provided with a countersunk hole and a limiting hole.

The countersunk hole and the limiting hole are coaxial and communicated.

A diameter of the countersunk hole is greater than or equal to a diameter of the protruding head, and a diameter of the limiting hole is smaller than a diameter of the protruding head.

The plug head and/or the protruding head have plasticity.

In one optional embodiment, an end of the plug head inserted into the inner tube is provided with a tapered head, wherein the tapered head is coaxial with the limiting hole.

Along a pulling direction of the traction member, an outer diameter of the tapered head decreases gradually.

In one optional embodiment, a distal end of the plug head is provided with a first convex ring. The first convex ring is located on a side of the inner tube away from the support, and an outer diameter of the first convex ring is greater than an inner diameter of the inner tube.

In one optional embodiment, the lock-cut mechanism also includes a suture traction component, wherein the suture traction component sequentially passes through a gap between the plug head and the inner tube, the first incision, and the second incision. A distal end of the suture traction component is provided with a coil.

In a second aspect, the medical suturing device provided by the present disclosure includes: an anchoring mechanism, a winding mechanism, and the lock-cut mechanism described in the first aspect.

The anchoring mechanism is configured to anchor the suture to the tissue to be sutured.

The suture sequentially passes through the gap between the plug head and the inner tube, the first incision, and the second incision, and the suture extends to the winding mechanism.

The winding mechanism is configured to pull the suture.

The embodiments of the present disclosure provide beneficial effects as follows. The inner tube is detachably connected to the support. The plug head is inserted into the inner tube, and the outer tube is sleeved on the inner tube and the support. The traction member passes through the outer tube, the inner tube, and the plug head, and a distal end of the traction member is provided with a protruding head. A side wall of the inner tube is provided with a first incision, and a side wall of the outer tube is provided with a second incision. By pulling the traction member, the locking and cutting operation of the suture can be realized, which allows the support to be disengaged from the inner tube and the outer tube to be confined to the support. This not only maintains the stability of the inner tube and the outer tube before the locking and cutting but also prevents falling off of the outer tube after the locking and cutting are completed. The compactness of the structure of the lock-cut mechanism is enhanced, which is conducive to reducing the radial dimension of the lock-cut mechanism, thereby allowing the lock-cut mechanism to pass through the endoscopic forceps channel more smoothly.

To make the above objectives, features, and advantages of the present disclosure more evident and comprehensible, the following preferred embodiments are described in detail with the drawings.

BRIEF DESCRIPTION OF DRAWINGS

In order to more clearly illustrate the specific embodiments of the present disclosure or the technical solution in the correlation technique, the drawings required to be used in the description of the specific embodiment or correlation technique will be briefly introduced as follows. Obviously, the drawings described below are some embodiments of the present disclosure. Those skilled in the art, without paying inventive labor, may also obtain other drawings according to these drawings.

Figure 1:
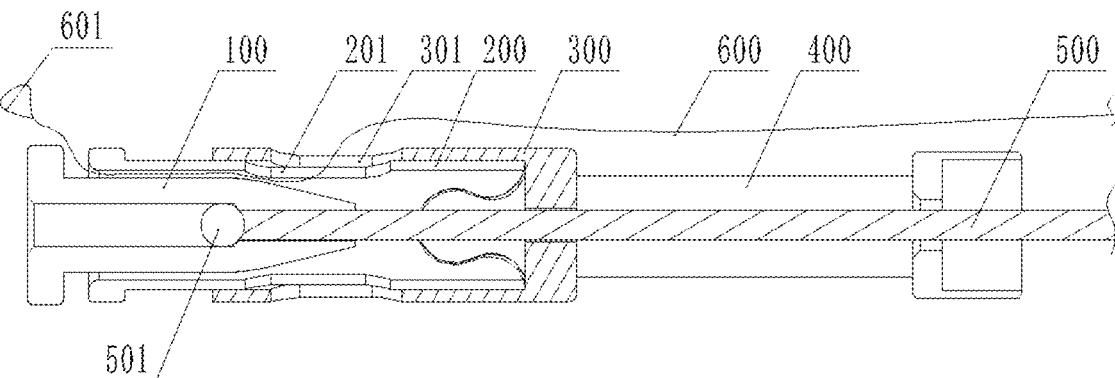
FIG. 1 is a sectional view of a lock-cut mechanism in a first phase of pulling a traction member provided by the embodiments of the present disclosure.

Reference numerals: 100—plug head; 101—countersunk hole; 102—limiting hole; 103—tapered head; 104—first convex ring; 200—inner tube; 201—first incision; 202—first inserting—connection part; 203—second convex ring; 300—outer tube; 301—second incision; 302—first axial socket; 303—second axial socket; 310—crossbeam; 311—through hole; 400—support; 401—second inserting-connection part; 402—snapping part; 410—first arm rod; 420—second arm rod; 430—base; 500—traction member; 501—protruding head; 600—suture traction component; 601—coil.

DETAILED DESCRIPTION OF EMBODIMENTS

A clear and complete description of the technical solutions of the present disclosure will be given below in connection with the drawings. Obviously, the described embodiments are part of the embodiments of the present disclosure, not all of the embodiments. Based on the embodiments of the present disclosure, all other embodiments obtained by those skilled in the art without inventive effort shall fall within the protection scope of the present disclosure.

In the description of the present disclosure, it should be noted that the terms such as "center", "top", "bottom", "left", "right", "vertical", "horizontal", "inside", and "outside" indicate orientations or positional relationships based on the orientations or positional relationships shown in the drawings, which are merely for the convenience of describing the present disclosure and simplifying the description and are not intended to indicate or imply that the referenced device or element must have a specific orientation, be constructed in a specific orientation, or operate in a specific orientation. Therefore, they should not be construed as limitations on the present disclosure. In addition, the terms "first", "second" and "third" are used for descriptive purposes only and are not to be construed as indicating or implying relative importance.

In the description of the present disclosure, it is important to note that unless otherwise clearly stipulated and limited, the terms "mount", "interconnect", and "connect" should be understood in a broad sense. For example, it can be a fixed connection, a detachable connection, or an integral connection; it can be a mechanical connection or an electrical connection; and it can be a direct connection, an indirect connection through an intermediary, or an internal communication between two components. In the text, "distal end" and "proximal end" are referenced from the perspective of the operator. The end of the product and its components that are away from the operator is referred to as the distal end, and the end of the product and its components that are closer to the operator is referred to as the proximal end. Those of ordinary skill in the art can understand the meanings of the above terms in the present disclosure according to specific situations.

As shown in FIGS. 1, 2, 3, and 4, the lock-cut mechanism provided in the embodiments of the present disclosure includes: a plug head 100, an inner tube 200, an outer tube 300, a support 400, and a traction member 500. The inner tube 200 is detachably connected to the support 400. The plug head 100 is inserted into the inner tube 200, and the outer tube 300 is sleeved on the inner tube 200 and the support 400. The traction member 500 passes through the outer tube 300, the inner tube 200, and the plug head 100, and a distal end of the traction member 500 is provided with a protruding head 501. A side wall of the inner tube 200 is provided with a first incision 201, and a side wall of the outer tube 300 is provided with a second incision 301.

Referring to FIG. 1, in a first phase of pulling the traction member 500, the first incision 201 and the second incision 301 are aligned to each other, and the protruding head 501 fits with the plug head 100 and drives the plug head 100 to move inside the inner tube 200. The suture can be clamped between the plug head 100 and the inner tube 200.

Figure 2:
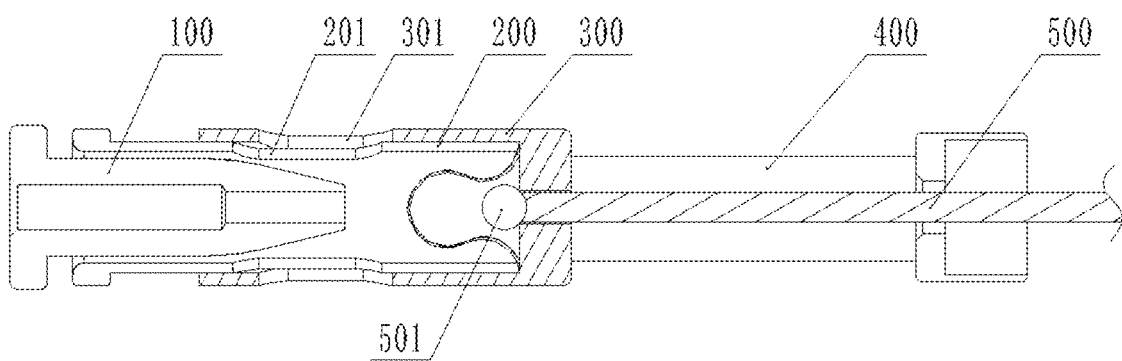
FIG. 2 is a sectional view of the lock-cut mechanism in a second phase of pulling the traction member provided by the embodiments of the present disclosure.

Referring to FIG. 2, in a second phase of pulling the traction member 500, the protruding head 501 or the plug head 100 is deformed, the protruding head 501 disengages from the plug head 100, and the protruding head 501 abuts the outer tube 300 and drives the outer tube 300 to move in a axial direction relative to the inner tube 200, thus causing the first incision 201 to misalign with the second incision 301. The suture extending outward from the first incision 201 and the second incision 301 can be cut by the misaligned first incision 201 and second incision 301, thereby removing the excess portion of the suture.

Figure 3:
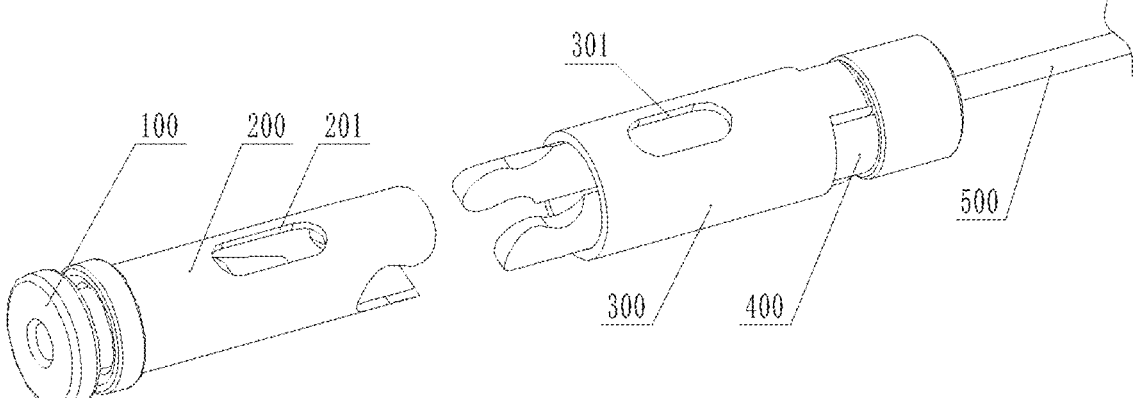
FIG. 3 is a schematic view of the lock-cut mechanism in a third phase of pulling the traction member provided by the embodiments of the present disclosure.

Referring to FIG. 3, in a third phase of pulling the traction member 500, the traction member 500 drives the outer tube 300 and allows the outer tube 300 to be sleeved onto the support 400, and the support 400 separates from the inner tube 200. In this phase, the plug head 100 and the inner tube 200, which clamp the suture, are left at the sutured wound surface. The traction member 500 drives the outer tube 300 to move towards the proximal end, and the outer tube 300 drives the support 400 to be withdrawn. The support 400 disengages from the inner tube 200 under the external force, thus allowing the traction member 500, the outer tube 300, and the support 400 to be withdrawn simultaneously.

As shown in FIGS. 1, 2, and 3, in the first phase and second phase, the outer tube 300 is sleeved on the inner tube 200. In the third phase, the outer tube 300 is sleeved on the support 400. Thus, throughout the entire process, the outer tube 300 will not be dislodged, thus reducing the risk of medical accidents.

As shown in FIGS. 1, 2, 3, 7, 8, and 9, in the embodiment of the present disclosure, the inner tube 200 is provided with a first inserting-connection part 202, and the support 400 is provided with a second inserting-connection part 401 adapted to the first inserting-connection part 202.

The first inserting-connection part 202 and the second inserting-connection part 401, one of which is configured as a slot and the other of which is configured as a protruding part adapted to the slot, enable the inner tube 200 to be connected to the support 400 through the cooperation of the first inserting-connection part 202 and the second inserting-connection part 401.

Additionally, the first inserting-connection part 202 and the second inserting-connection part 401 can fit together by an interference fit. When an external force pulls the support 400 back, the pulling force can cause the first inserting-connection part 202 and the second inserting-connection part 401 to separate from each other.

In optional embodiments, the first inserting-connection part 202 and the second inserting-connection part 401, one of which is provided with a protruding head and the other of which is provided with a snapping groove adapted to the protruding head, enable the inner tube 200 to be connected to the support 400 by inserting the protruding head into the snapping groove. When an external force drives the support 400 to be withdrawn, the first inserting-connection part 202 and the second inserting-connection part 401 disengage from each other, thereby separating the support 400 from the inner tube 200.

Figure 4:
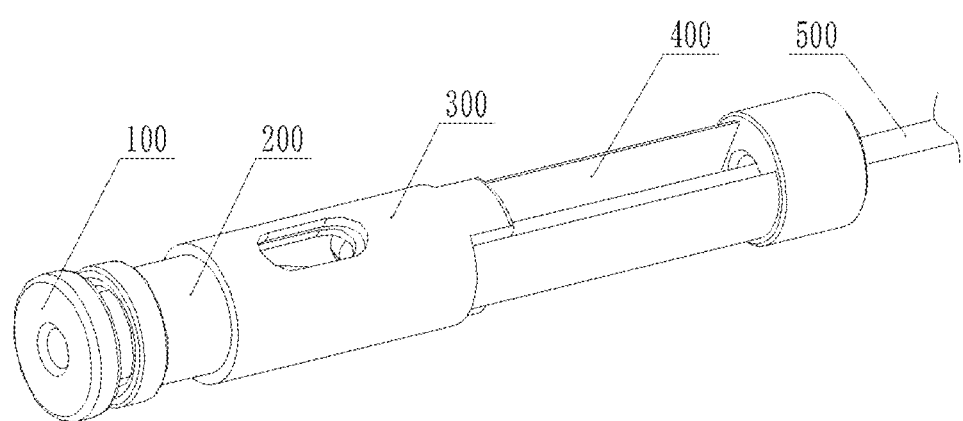
FIG. 4 is a schematic view of the lock-cut mechanism provided by the embodiments of the present disclosure.
Figure 5:
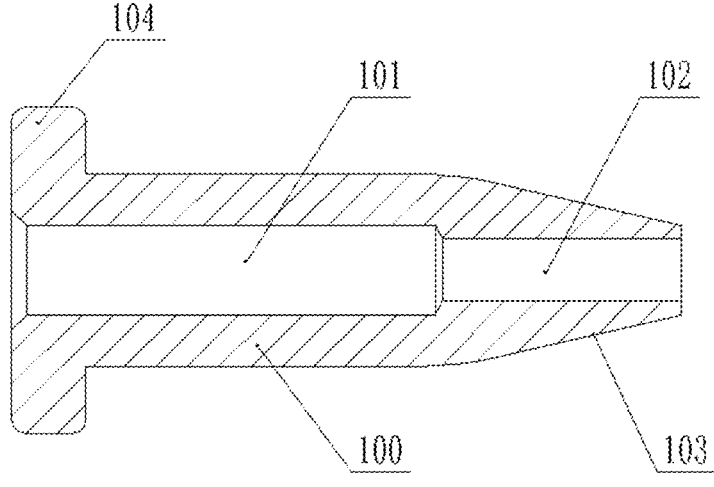
FIG. 5 is a sectional view of a plug head of the lock-cut mechanism provided by the embodiments of the present disclosure.
Figure 6:
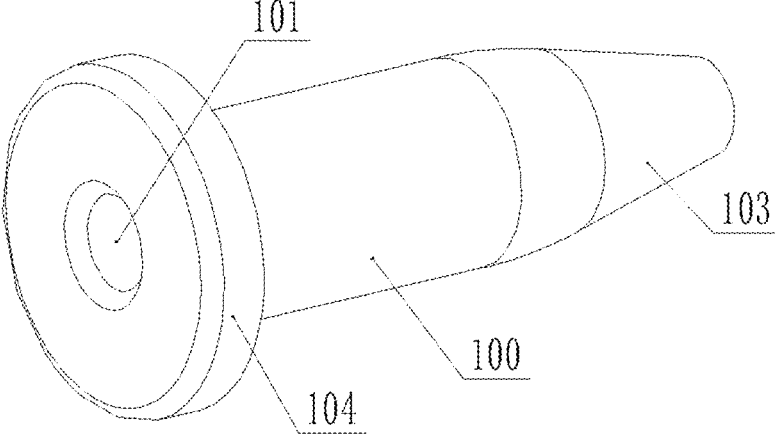
FIG. 6 is a schematic view of the plug head of the lock-cut mechanism provided by the embodiments of the present disclosure.
Figures 7, 8:
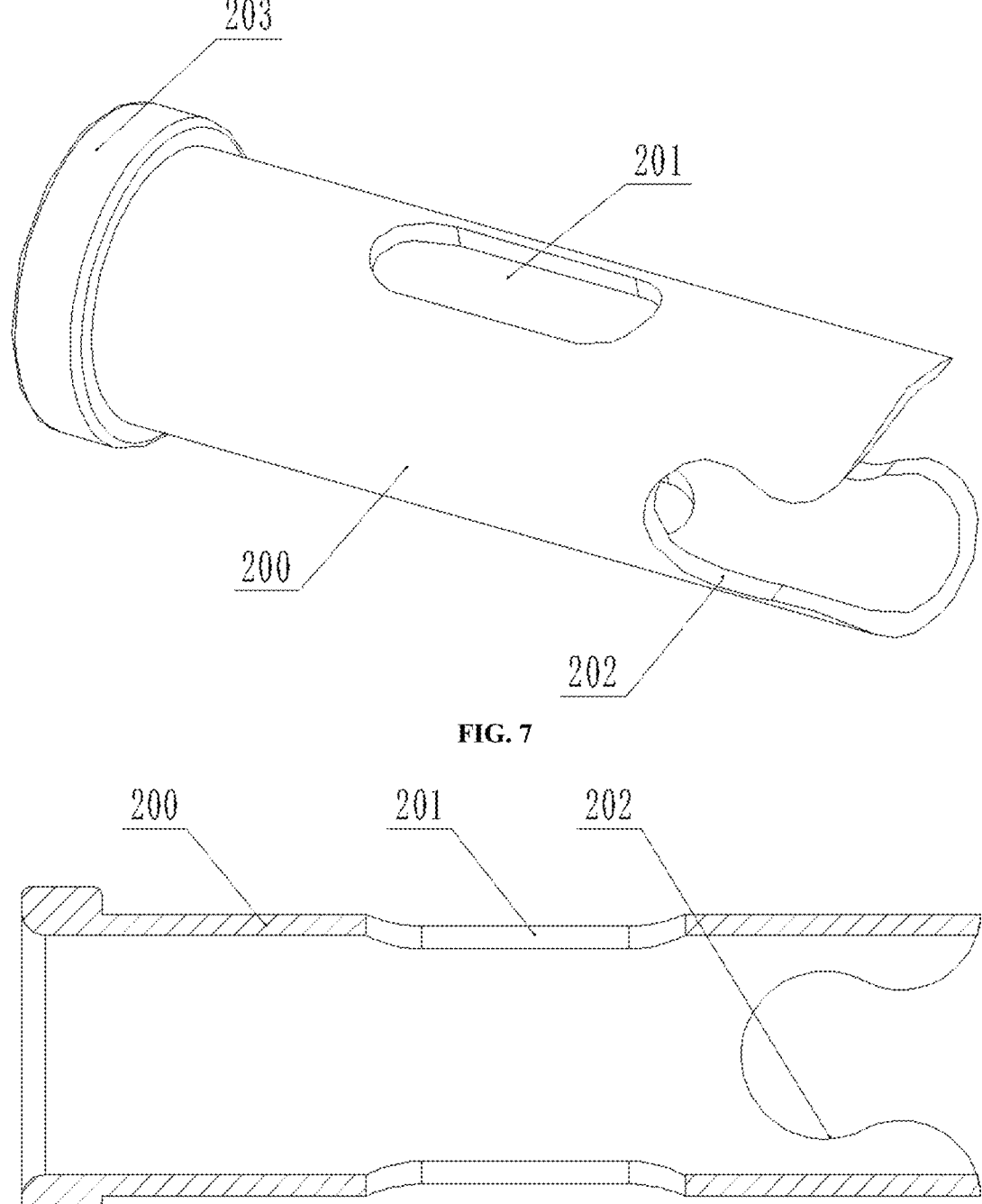
FIG. 7 is a schematic view of an inner tube of the lock-cut mechanism provided by the embodiments of the present disclosure.
FIG. 8 is a sectional view of the inner tube of the lock-cut mechanism provided by the embodiments of the present disclosure.
Figure 9:
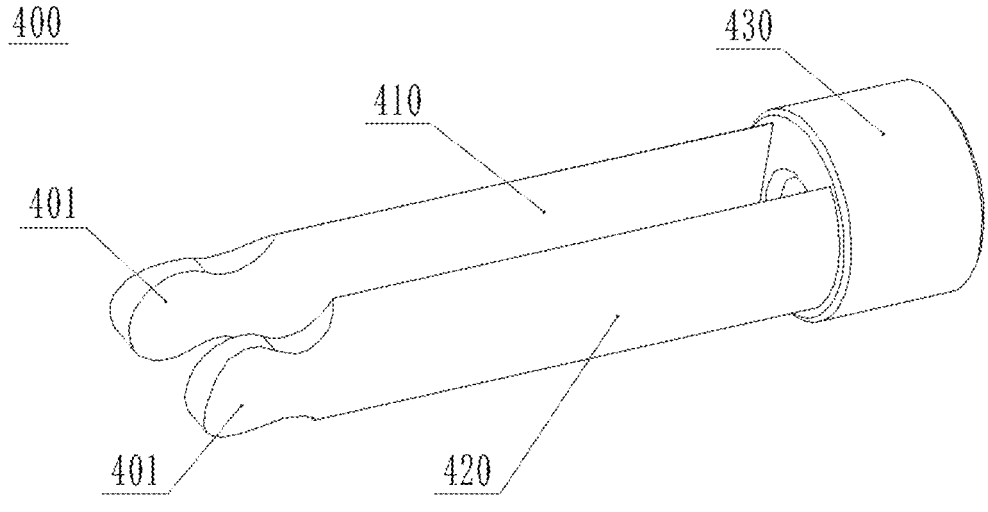
FIG. 9 is a schematic view of a support of the lock-cut mechanism provided by the embodiments of the present disclosure.
Figure 10:
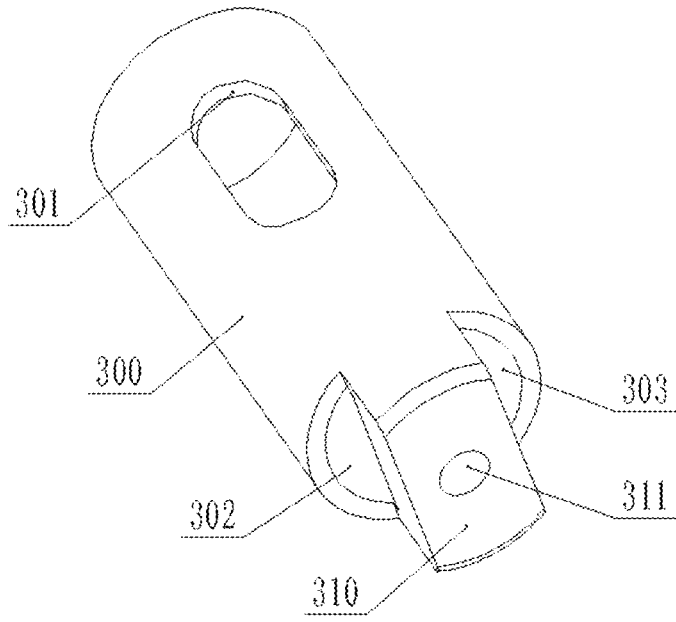
FIG. 10 is a schematic view of an outer tube of the lock-cut mechanism provided by the embodiments of the present disclosure.
Figure 11:
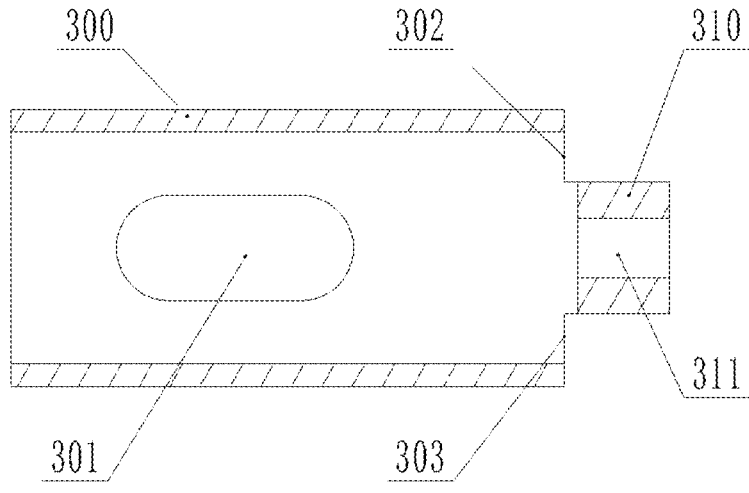
FIG. 11 is a sectional view of the outer tube of the lock-cut mechanism provided by the embodiments of the present disclosure.
Figure 12:
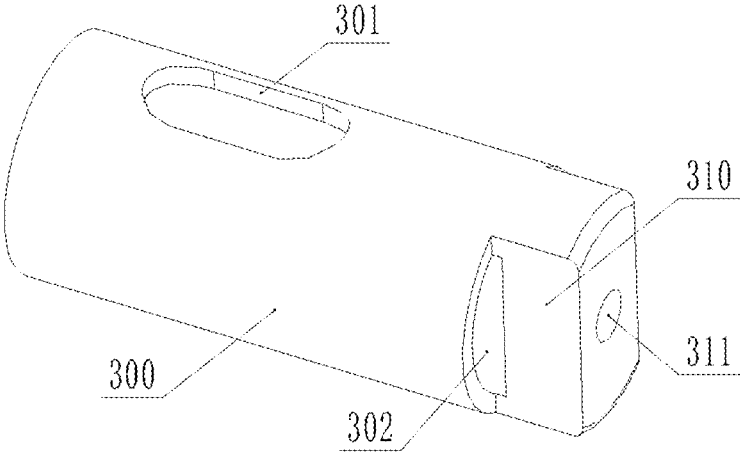
FIG. 12 is a schematic view of the outer tube of the lock-cut mechanism from another angle provided by the embodiments of the present disclosure.

As shown in FIGS. 4, 7, and 9, the support 400 is provided with a first arm rod 410 and a second arm rod 420, wherein the first arm rod 410 and the second arm rod 420 are substantially parallel. Both the first arm rod 410 and the second arm rod 420 are provided with second inserting-connection parts 401.

The proximal end of the inner tube 200 is provided with two first inserting-connection parts 202, and the two first inserting-connection parts 202 are provided at intervals along a circumference of the inner tube 200. The end portions of the first arm rod 410 and the second arm rod 420 are respectively fitted with the first inserting-connection part 202 through the second inserting-connection part 401, thereby enabling a detachable connection between the support 400 and the inner tube 200.

As shown in FIGS. 4, 9, 10, 11, and 12, a proximal end of the outer tube 300 is provided with a crossbeam 310, wherein the crossbeam 310 is provided with a through hole 311 coaxial with the outer tube 300. The traction member 500 passes through the through hole 311, and a diameter of the protruding head 501 is larger than a diameter of the through hole 311. The outer tube 300 is provided with a first axial socket 302 and a second axial socket 303, wherein the first arm rod 410 and the second arm rod 420 pass through the first axial socket 302 and the second axial socket 303 in one-to-one correspondence.

In the third phase of pulling the traction member 500, the protruding head 501 abuts the crossbeam 310, subsequently drives the protruding head 501 to push against the support 400, and enables the support 400 to separate from the inner tube 200, thereby enabling the traction member 500, the outer tube 300, and the support 400 to be withdrawn simultaneously.

Further, both the first arm rod 410 and the second arm rod 420 are connected to a base 430, the crossbeam 310 is in sliding fit between the first arm rod 410 and the second arm rod 420, and the crossbeam 310 and the base 430 are arranged opposite to each other. The base 430 is provided with a through hole. The traction member 500 passes through the through hole and extends outward. When the protruding head 501 drives the outer tube 300 to move towards the proximal end, the crossbeam 310 pushes against the base 430, thereby forcing the second inserting-connection part 401 to disengage from the first inserting-connection part 202.

Figure 13:
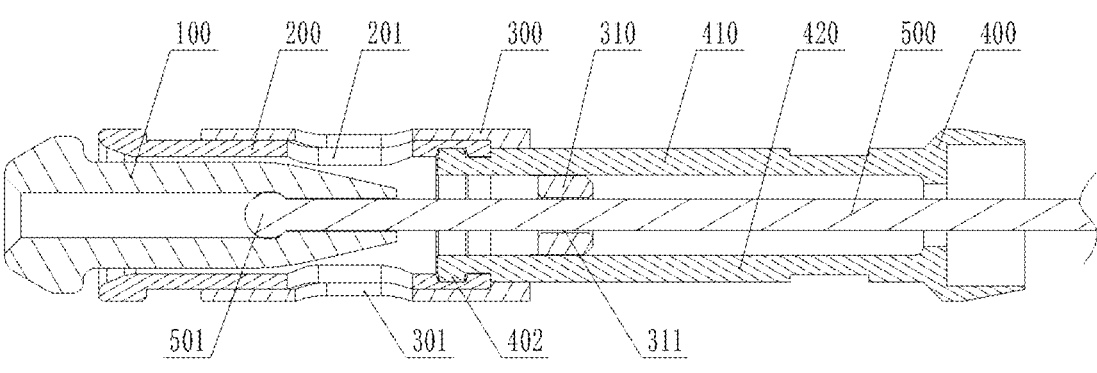
FIG. 13 is another sectional view of the lock-cut mechanism in the first phase of pulling the traction member provided by the embodiments of the present disclosure.
Figure 14:
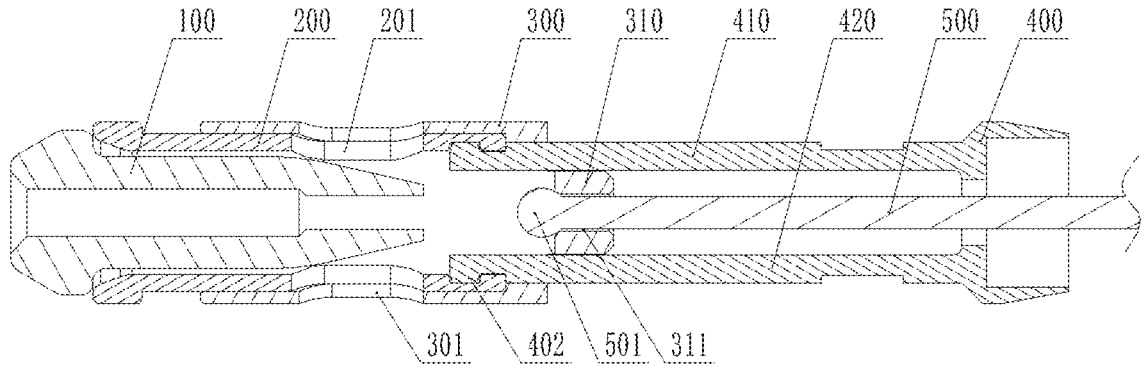
FIG. 14 is another sectional view of the lock-cut mechanism in the second phase of pulling the traction member provided by the embodiments of the present disclosure.
Figure 15:
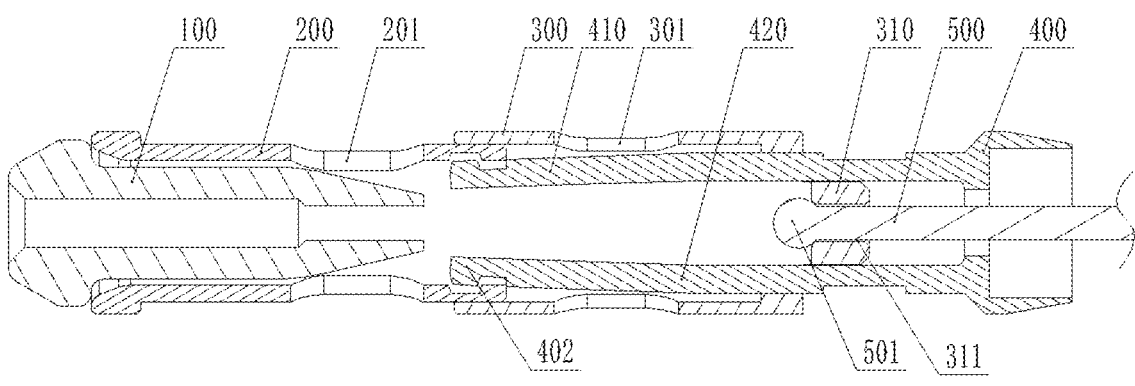
FIG. 15 is another schematic view of the lock-cut mechanism in the third phase of pulling the traction member provided by the embodiments of the present disclosure.

As shown in FIGS. 13, 14, and 15, in optional embodiments, the support 400 is provided with a first arm rod 410 and a second arm rod 420, with at least one of the first arm rod 410 and the second arm rod 420 provided with a snapping part 402 that fits the inner tube 200. The first arm rod 410 and the second arm rod 420 have a tendency to be inclined in a direction close to an axis of the inner tube 200, thus causing the snapping part 402 to disengage from the inner tube 200. The outer tube 300 is connected to the crossbeam 310, where the crossbeam 310 is positioned between the first arm rod 410 and the second arm rod 420.

The support 400, which is integrally molded and is provided with the first arm rod 410 and the second arm rod 420, is provided. Moreover, in a natural state, from the proximal end to the distal end, the first arm rod 410 and the second arm rod 420 are inclined in a direction close to the axis of the inner tube 200. Referring to FIGS. 13 and 4, in the first and second phases of pulling the traction member 500, the crossbeam 310 is located between the first arm rod 410 and the second arm rod 420 and at a position close to the distant end. Therefore, the inclination tendency of the first arm rod 410 and the second arm rod 420 is counteracted by the support of the crossbeam 310, thus allowing the snapping part 402 to fit with the inner wall of the inner tube 200. One of the first arm rod 410 and the second arm rod 420 can be provided with the snapping part 402, or the snapping part 402 is provided on the first arm rod 410 and the second arm rod 420, respectively. In the first and second phases of pulling the traction member 500, the crossbeam 310 supports the first arm rod 410 and the second arm rod 420, which can allow the snapping part 402 to abut against the inner wall of the inner tube 200 in a direction away from the axis of the inner tube 200. Thereby, the first arm rod 410 and the second arm rod 420 are distended in the inner tube 200. To enhance the stability of the connection, the inner wall of the inner tube 200 can be machined with a snapping groove or a protrusion that fits the snapping part 402, thus improving the stability of the connection between the inner tube 200 and the support 400 in the state of engagement.

Further, the crossbeam 310 is provided with a through hole 311. The traction member 500 passes through the through hole 311. A diameter of the protruding head 501 is larger than a diameter of the through hole 311. During the third phase of pulling the traction member 500, the protruding head 501 abuts the crossbeam 310, thus causing the outer tube 300, along with the traction member 500, to slide relative to the support 400.

Additionally, the crossbeam 310 is preferably arranged at the proximal end of the outer tube 300. In the third phase of pulling the traction member 500, the crossbeam 310 can move to a position closer to the proximal end between the first arm rod 410 and the second arm rod 420, thus allowing the distal ends of the first arm rod 410 and the second arm rod 420 to be fully inclined in a direction close to the axis of the inner tube 200. This ensures that the snapping part 402 completely disengages from the inner tube 200. Subsequently, by continuing to pull the traction member 500 towards the proximal end, the outer tube 300 is sleeved on the support 400, and both the outer tube 300 and the support 400 can be pulled and removed along with the traction member 500.

In optional embodiments, grooves can be provided on the inner sides of the first arm rod 410 and the second arm rod

420, which are closer to the proximal end, respectively. When the traction member 500 pulls the outer tube 300 until the crossbeam 310 and the groove are opposite to each other, the first arm rod 410 and the second arm rod 420 are inclined in a direction close to the axis of the inner tube 200, causing the crossbeam 310 to insert into the grooves on the inner sides of the first arm rod 410 and the second arm rod 420. This disengages the snapping part 402 from the inner tube 200 and secures the first arm rod 410 and the second arm rod 420 to the crossbeam 310. Subsequently, by continuing to pull the traction member 500, the outer tube 300 and the support 400 can be removed together.

As shown in FIGS. 1, 2, 3, 4, and 5, the plug head 100 is provided with a countersunk hole 101 and a limiting hole 102. The countersunk hole 101 and the limiting hole 102 are coaxial and communicated to each other. A diameter of the countersunk hole 101 is greater than or equal to a diameter of the protruding head 501, and a diameter of the limiting hole 102 is smaller than a diameter of the protruding head 501. The plug head 100 and/or the protruding head 501 have plasticity. One of the plug head 100 and the protruding head 501 is configured as a plastic structure, or both the plug head 100 and the protruding head 501 are configured as plastic structures.

In the first phase, the protruding head 501 is located inside the countersunk hole 101. The diameter of the limiting hole 102 is smaller than the diameter of the protruding head 501, which can prevent the protruding head 501 from moving toward the proximal end relative to the plug head 100. Thus, the traction member 500 can drive the plug head 100 to insert into the inner tube 200. In the second phase, the suture is clamped between the plug head 100 and the inner tube 200. The plug head 100 can no longer move toward the proximal end relative to the inner tube 200. Under the pulling force, at least one of the plug head 100 and the protruding head 501 undergoes plastic deformation, and the protruding head 501 slides along the limiting hole 102 until it disengages from the plug head 100.

As shown in FIGS. 1, 2, 5, and 6, an end of the plug head 100 inserted into the inner tube 200 is provided with a tapered head 103, wherein the tapered head 103 is coaxial with the limiting hole 102. Along a pulling direction of the traction member 500, an outer diameter of the tapered head 103 decreases gradually. The pulling direction is from the distal end to the proximal end. In the first phase, the traction member 500 can drive the plug head 100 to insert into the inner tube 200. Guiding through the tapered head 103 allows the plug head 100 to be coaxial with the inner tube 200 and clamps the suture between the plug head 100 and the inner tube 200.

Further, a distal end of the plug head 100 is provided with a first convex ring 104. The first convex ring 104 is located on a side of the inner tube 200 away from the support 400, and an outer diameter of the first convex ring 104 is greater than an inner diameter of the inner tube 200. The first convex ring 104 can restrict the stroke distance of the plug head 100 inserted into the inner tube 200, and the suture can be clamped between the first convex ring 104 and the inner tube 200.

Furthermore, an end of the inner tube 200 facing the first convex ring 104 is provided with a second convex ring 203. A first suture clamping gap is formed between the first convex ring 104 and the second convex ring 203, and a second suture clamping gap is formed between the outer surface of the inner tube 200 and the outer surface of the plug head 100. The suture can be clamped between the first convex ring 104 and the second convex ring 203. By affixing the first convex ring 104 and the second convex ring 203 together, the contact area between the inner tube 200 and the plug head 100 at the position clamping the suture is increased.

As shown in FIG. 1, the lock-cut mechanism also includes a suture traction component 600, wherein the suture traction component 600 sequentially passes through a gap between the plug head 100 and the inner tube 200, the first incision 201, and the second incision 301. A distal end of the suture traction component 600 is provided with a coil 601. When operating the suture traction component, the suture passes through the coil 601, and the suture traction component 600 is then pulled toward the proximal end. Therefore, the suture is driven to sequentially pass through the gap between the plug head 100 and the inner tube 200, the first incision 201, and the second incision 301.

The embodiments of the present disclosure provide a medical suturing device, including: an anchoring mechanism, a winding mechanism, and the lock-cut mechanism described in the above embodiments. The anchoring mechanism anchors the suture to the tissue to be sutured. The suture sequentially passes through the gap between the plug head 100 and the inner tube 200, the first incision 201, and the second incision 301, and the suture extends to the winding mechanism. The winding mechanism pulls the suture.

In the embodiments of the present disclosure, the anchoring mechanism applies an anchor head to connect the suture and the anchor head is inserted into the tissue to be sutured. The suture, pulled by using the suture traction component 600 or the thread hook, sequentially passes through the gap between the plug head 100 and the inner tube 200, the first incision 201, and the second incision 301, and the suture is enabled to extend to the winding mechanism. The winding mechanism winds and tightens the suture by a thread wheel. Once the suture is tightened, the traction member 500 is pulled, which drives the plug head 100 to insert into the inner tube 200. Thus, the suture is clamped and secured between the plug head 100 and the inner tube 200. Subsequently, with the further pulling on the traction member 500, the protruding head 501 slips away from the plug head 100, and the traction member 500 drives the outer tube 300 to slide relative to the inner tube 200. Therefore, the suture is cut off by misaligning the first incision 201 with the second incision 301. Then, by continuing to pull the traction member 500, the outer tube 300 pushes against the support 400 and drives the support 400 to disengage from the inner tube 200 so that the traction member 500, the outer tube 300, and the support 400 can be withdrawn together.

Finally, it should be noted that the above embodiments are only used to illustrate the technical solution of the present disclosure, not to limit it. Notwithstanding the detailed description of the present disclosure with reference to the foregoing embodiments, it should be understood by those of ordinary skill in the art that one may still modify the technical solution described in the preceding embodiments, or make equivalent substitutions for some or all of the technical features therein. However, these modifications or substitutions do not depart the essence of the corresponding technical solution from the scope of the technical solution of the embodiments of the present disclosure.

What is claimed is:

1. A lock-cut mechanism, comprising a plug head, an inner tube, an outer tube, a support, and a traction member, wherein
the inner tube is detachably connected to the support;

the plug head is inserted into the inner tube, and the outer tube is sleeved on the inner tube and the support;

the traction member passes through the outer tube, the inner tube, and the plug head, and a distal end of the traction member is provided with a protruding head;

a side wall of the inner tube is provided with a first incision, and a side wall of the outer tube is provided with a second incision;

in a first phase of pulling the traction member, the first incision and the second incision are aligned, and the protruding head fits with the plug head and drives the plug head to move inside the inner tube;

in a second phase of pulling the traction member, the protruding head disengages from the plug head, and the protruding head abuts the outer tube and drives the outer tube to move in an axial direction relative to the inner tube, thus causing the first incision to misalign with the second incision; and in a third phase of pulling the traction member, the traction member drives the outer tube and allows the outer tube to be sleeved onto the support, and the support separates from the inner tube.

2. The lock-cut mechanism according to claim 1, wherein the inner tube is provided with a first inserting-connection part, and the support is provided with a second inserting-connection part adapted to the first inserting-connection part.

3. The lock-cut mechanism according to claim 2, wherein the support is provided with a first arm rod and a second arm rod, and the first arm rod and the second arm rod are substantially parallel; and both the first arm rod and the second arm rod are provided with the second inserting-connection part.

4. The lock-cut mechanism according to claim 3, wherein a proximal end of the outer tube is provided with a cross-beam, and the crossbeam is provided with a through hole coaxial with the outer tube;

the traction member passes through the through hole, and a diameter of the protruding head is larger than a diameter of the through hole; and the outer tube is provided with a first axial socket and a second axial socket, wherein the first arm rod and the second arm rod pass through the first axial socket and the second axial socket in one-to-one correspondence.

5. The lock-cut mechanism according to claim 4, wherein both the first arm rod and the second arm rod are connected to a base; the crossbeam is in sliding fit between the first arm rod and the second arm rod; and the crossbeam and the base are arranged opposite to each other.

6. The lock-cut mechanism according to claim 1, wherein the support is provided with a first arm rod and a second arm rod, with at least one of the first arm rod and the second arm rod provided with a snapping part that fits the inner tube; the first arm rod and the second arm rod have a tendency to be inclined in a direction close to an axis of the inner tube, thus causing the snapping part to disengage from the inner tube; and the outer tube is connected to a crossbeam, wherein the crossbeam is located between the first arm rod and the second arm rod.

7. The lock-cut mechanism according to claim 6, wherein the crossbeam is provided with a through hole; the traction member passes through the through hole; and a diameter of the protruding head is larger than a diameter of the through hole; and in the third phase of pulling the traction member, the protruding head abuts the crossbeam, thus causing the outer tube, along with the traction member, to slide relative to the support.

8. The lock-cut mechanism according to claim 1, wherein the plug head is provided with a countersunk hole and a limiting hole;

the countersunk hole and the limiting hole are coaxial and communicated;

a diameter of the countersunk hole is greater than or equal to a diameter of the protruding head, and a diameter of the limiting hole is smaller than a diameter of the protruding head; and the plug head and/or the protruding head have plasticity.

9. The lock-cut mechanism according to claim 8, wherein an end of the plug head inserted into the inner tube is provided with a tapered head, and the tapered head is coaxial with the limiting hole; and along a pulling direction of the traction member, an outer diameter of the tapered head decreases gradually.

10. The lock-cut mechanism according to claim 8, wherein a distal end of the plug head is provided with a first convex ring; the first convex ring is located on a side of the inner tube away from the support; and an outer diameter of the first convex ring is greater than an inner diameter of the inner tube.

11. The lock-cut mechanism according to claim 1, wherein the lock-cut mechanism further comprises a suture traction component; and the suture traction component sequentially passes through a gap between the plug head and the inner tube, the first incision, and the second incision.

12. A medical suturing device, comprising: an anchoring mechanism, a winding mechanism, and the lock-cut mechanism according to claim 1, wherein the anchoring mechanism is configured to anchor a suture to a tissue to be sutured;

the suture sequentially passes through a gap between the plug head and the inner tube, the first incision, and the second incision, and the suture extends to the winding mechanism; and the winding mechanism is configured to pull the suture.

13. The medical suturing device according to claim 12, wherein the inner tube is provided with a first inserting-connection part, and the support is provided with a second inserting-connection part adapted to the first inserting-connection part.

14. The medical suturing device according to claim 13, wherein the support is provided with a first arm rod and a second arm rod, and the first arm rod and the second arm rod are substantially parallel; and both the first arm rod and the second arm rod are provided with the second inserting-connection part.

15. The medical suturing device according to claim 14, wherein a proximal end of the outer tube is provided with a crossbeam, and the crossbeam is provided with a through hole coaxial with the outer tube;

the traction member passes through the through hole, and a diameter of the protruding head is larger than a diameter of the through hole; and the outer tube is provided with a first axial socket and a second axial socket, wherein the first arm rod and the second arm rod pass through the first axial socket and the second axial socket in one-to-one correspondence.

16. The medical suturing device according to claim 15, wherein both the first arm rod and the second arm rod are connected to a base; the crossbeam is in sliding fit between the first arm rod and the second arm rod; and the crossbeam and the base are arranged opposite to each other.

17. The medical suturing device according to claim 12, wherein the support is provided with a first arm rod and a second arm rod, with at least one of the first arm rod and the second arm rod provided with a snapping part that fits the inner tube; the first arm rod and the second arm rod have a tendency to be inclined in a direction close to an axis of the inner tube, thus causing the snapping part to disengage from the inner tube; and the outer tube is connected to a crossbeam, wherein the crossbeam is located between the first arm rod and the second arm rod.

18. The medical suturing device according to claim 17, wherein the crossbeam is provided with a through hole; the traction member passes through the through hole; and a diameter of the protruding head is larger than a diameter of the through hole; and in the third phase of pulling the traction member, the protruding head abuts the crossbeam, thus causing the outer tube, along with the traction member, to slide relative to the support.

19. The medical suturing device according to claim 12, wherein the plug head is provided with a countersunk hole and a limiting hole;

the countersunk hole and the limiting hole are coaxial and communicated;

a diameter of the countersunk hole is greater than or equal to a diameter of the protruding head, and a diameter of the limiting hole is smaller than a diameter of the protruding head; and the plug head and/or the protruding head have plasticity.

20. The medical suturing device according to claim 19, wherein an end of the plug head inserted into the inner tube is provided with a tapered head, and the tapered head is coaxial with the limiting hole; and along a pulling direction of the traction member, an outer diameter of the tapered head decreases gradually.

* * * * *